(12) United States Patent
Henninger et al.

(10) Patent No.: US 12,078,531 B2
(45) Date of Patent: Sep. 3, 2024

(54) DEVICES, SYSTEMS, AND METHODS FOR CALIBRATING AN OPTICAL MEASUREMENT DEVICE

(71) Applicant: HI LLC, Los Angeles, CA (US)

(72) Inventors: Michael Henninger, Austin, TX (US); Isai Olvera, South Portland, ME (US); Han Yong Ban, Los Angeles, CA (US); Ryan Field, Culver City, CA (US)

(73) Assignee: HI LLC, Culver City, CA (US)

( * ) Notice: Subject to any disclaimer, the term of this patent is extended or adjusted under 35 U.S.C. 154(b) by 317 days.

(21) Appl. No.: 17/729,593

(22) Filed: Apr. 26, 2022

(65) Prior Publication Data
US 2023/0035935 A1 Feb. 2, 2023

Related U.S. Application Data

(60) Provisional application No. 63/226,618, filed on Jul. 28, 2021.

(51) Int. Cl.
*G01J 1/04* (2006.01)
*G01J 1/16* (2006.01)
*G01J 1/44* (2006.01)

(52) U.S. Cl.
CPC ........... *G01J 1/0474* (2013.01); *G01J 1/0422* (2013.01); *G01J 2001/1668* (2013.01); *G01J 2001/444* (2013.01)

(58) Field of Classification Search
CPC ........ G01J 1/00; G01J 1/02; G01J 1/04; G01J 1/0407; G01J 1/0422; G01J 1/0474;
(Continued)

(56) References Cited

U.S. PATENT DOCUMENTS 5,853,370 A 12/1998 Chance et al.
6,240,309 B1 5/2001 Yamashita et al.
(Continued)

FOREIGN PATENT DOCUMENTS

JP H10221452 A * 8/1998 ............... G01T 1/00
WO 2018033751 2/2018

OTHER PUBLICATIONS

Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680, Oct. 29, 2018.
(Continued)

*Primary Examiner* — Hoai-An D. Nguyen
(74) *Attorney, Agent, or Firm* — ALG Intellectual Property, LLC

(57) ABSTRACT

An illustrative calibration member made from a material that scatters light may be used to perform a calibration operation with respect to an optical measurement device having a plurality of light sources and a plurality of detectors distributed among a plurality of modules. The calibration member may form an exterior surface configured to support the optical measurement device and scatter photons of light emitted by the optical measurement device. The calibration operation may be performed based on arrival times of the scattered photons detected by the optical measurement device.

28 Claims, 17 Drawing Sheets

(58) Field of Classification Search
CPC ........ G01J 1/10; G01J 1/16; G01J 1/42; G01J 1/44; G01J 2001/1668; G01J 2001/444; A61B 5/00; A61B 5/0059; A61B 5/0075; A61B 5/1455; A61B 5/14551; A61B 5/14553; A61B 5/68; A61B 5/6801; A61B 5/6813; A61B 5/6814; A61B 2560/00; A61B 2560/02; A61B 2560/0223; A61B 2560/0238
USPC .............................. 324/600, 602, 605, 607
See application file for complete search history.

(56) References Cited

U.S. PATENT DOCUMENTS

| | | |
|---|---|---|
| 6,384,663 B2 | 5/2002 | Cova et al. |
| 6,556,149 B1* | 4/2003 | Reimer ............. H03K 17/9631 250/227.21 |
| 6,640,133 B2 | 10/2003 | Yamashita |
| 6,683,294 B1 | 1/2004 | Herbert et al. |
| 7,356,365 B2 | 4/2008 | Schurman |
| 7,547,872 B2 | 6/2009 | Niclass et al. |
| 7,774,047 B2 | 8/2010 | Yamashita et al. |
| 8,026,471 B2 | 9/2011 | Itzler |
| 8,078,250 B2 | 12/2011 | Chen et al. |
| 8,082,015 B2 | 12/2011 | Yodh et al. |
| 8,633,431 B2 | 1/2014 | Kim |
| 8,817,257 B2 | 8/2014 | Herve |
| 9,058,081 B2 | 6/2015 | Baxter |
| 9,076,707 B2 | 7/2015 | Harmon |
| 9,131,861 B2 | 9/2015 | Ince et al. |
| 9,316,735 B2 | 4/2016 | Baxter |
| 9,401,448 B2 | 7/2016 | Bienfang et al. |
| 9,419,635 B2 | 8/2016 | Kumar et al. |
| 9,442,201 B2 | 9/2016 | Schmand et al. |
| 9,529,079 B1 | 12/2016 | Droz |
| 9,574,936 B2 | 2/2017 | Heinonen |
| 9,946,344 B2 | 4/2018 | Ayaz et al. |
| D817,553 S | 5/2018 | Aaskov et al. |
| D825,112 S | 8/2018 | Saez |
| 10,158,038 B1 | 12/2018 | Do Valle et al. |
| 10,340,408 B1 | 7/2019 | Katnani |
| 10,424,683 B1 | 9/2019 | Do Valle |
| 10,515,993 B2 | 12/2019 | Field et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,912,504 B2 | 2/2021 | Nakaji |
| 11,006,876 B2 | 5/2021 | Johnson |
| 11,006,878 B2 | 5/2021 | Johnson |
| 11,096,620 B1 | 8/2021 | Seidman |
| 2007/0083097 A1 | 4/2007 | Fujiwara |
| 2009/0012402 A1 | 1/2009 | Mintz |
| 2011/0208675 A1 | 8/2011 | Shoureshi et al. |
| 2013/0342835 A1 | 12/2013 | Blacksberg |
| 2014/0191115 A1 | 7/2014 | Webster et al. |
| 2014/0217264 A1 | 8/2014 | Shepard |
| 2014/0275891 A1 | 9/2014 | Muehlemann et al. |
| 2015/0038811 A1 | 2/2015 | Asaka |
| 2015/0041625 A1 | 2/2015 | Dutton |
| 2015/0054111 A1 | 2/2015 | Niclass et al. |
| 2015/0077279 A1 | 3/2015 | Song |
| 2015/0150505 A1 | 6/2015 | Kaskoun et al. |
| 2015/0327777 A1 | 11/2015 | Kostic et al. |
| 2015/0364635 A1 | 12/2015 | Bodlovic et al. |
| 2017/0030769 A1 | 2/2017 | Clemens et al. |
| 2017/0052065 A1 | 2/2017 | Sharma et al. |
| 2017/0176596 A1 | 6/2017 | Shpunt et al. |
| 2017/0179173 A1 | 6/2017 | Mandai et al. |
| 2017/0202518 A1 | 7/2017 | Furman et al. |
| 2017/0281086 A1 | 10/2017 | Donaldson |
| 2017/0336326 A1* | 11/2017 | Sirat ................. G02B 21/0076 |
| 2017/0363467 A1 | 12/2017 | Clemens et al. |
| 2017/0367650 A1 | 12/2017 | Wallois |
| 2018/0014741 A1 | 1/2018 | Chou |
| 2018/0027196 A1 | 1/2018 | Yang et al. |
| 2018/0039053 A1 | 2/2018 | Kremer et al. |
| 2018/0070830 A1 | 3/2018 | Sutin et al. |
| 2018/0070831 A1 | 3/2018 | Sutin et al. |
| 2018/0089848 A1 | 3/2018 | Yang et al. |
| 2019/0113385 A1 | 4/2019 | Fukuchi |
| 2019/0175068 A1 | 6/2019 | Everdell |
| 2019/0355861 A1 | 11/2019 | Katnani |
| 2019/0363210 A1 | 11/2019 | Do Valle |
| 2019/0388018 A1 | 12/2019 | Horstmeyer |
| 2020/0060542 A1 | 2/2020 | Alford |
| 2020/0116838 A1 | 4/2020 | Erdogan |
| 2020/0196932 A1 | 6/2020 | Johnson |
| 2020/0253479 A1 | 8/2020 | Nurmikko |
| 2020/0315510 A1 | 10/2020 | Johnson |
| 2020/0337624 A1 | 10/2020 | Johnson |
| 2020/0390358 A1 | 12/2020 | Johnson |
| 2021/0259597 A1 | 8/2021 | Katnani et al. |
| 2021/0259614 A1 | 8/2021 | Ojeda et al. |
| 2021/0259619 A1 | 8/2021 | Seidman et al. |
| 2021/0259620 A1 | 8/2021 | Olvera et al. |
| 2021/0259632 A1 | 8/2021 | Seidman et al. |
| 2021/0259638 A1 | 8/2021 | Do Valle et al. |
| 2021/0263320 A1 | 8/2021 | Seidman et al. |
| 2021/0290066 A1* | 9/2021 | Field .................... A61B 5/6803 |
| 2021/0290069 A1* | 9/2021 | Sorgenfrei ........... A61B 5/4064 |
| 2021/0290146 A1* | 9/2021 | Sorgenfrei ........... A61B 5/4064 |
| 2021/0293614 A1* | 9/2021 | Field ..................... G01J 1/0238 |

OTHER PUBLICATIONS

Ban, et al., "Kernel Flow: a high channel count scalable TD-fNIRS system", https://www.spiedigitallibrary.org/conference-proceedings-of-spie Proc. of SPIE vol. 11663, 116630B doi: 10.1117/12. 2582888, Mar. 5, 2021.

Ban, et al., "Kernel Flow: a high channel count scalable time-domain functional near-infrared spectroscopy system", https://www.spiedigitallibrary.org/journals/Journal-of-Biomedical-Optics on Jan. 18, 2022.

Contini, et al., "Photon migration through a turbid slab described by a model based on diffusion approximation. I. Theory", Appl. Opt. 36(19), 4587 (1997).

Di Sieno, et al., "Probe-hosted large area silicon photomultiplier and high-throughput timing electronics for enhanced performance time-domain functional near-infrared spectroscopy", Biomed. Opt. Express 11(11), 6389 (2020).

Fishburn, et al., "Temporal Derivative Distribution Repair (TDDR): A motion correction method for fNIRS", Neuroimage. Jan. 1, 2019; 184: 171-179. doi:10.1016/j.neuroimage.2018.09.025.

Huppert, et al., "HomER: a review of time-series analysis methods for near-infrared spectroscopy of the brain", Appl. Opt. 48(10), D280 (2009).

Kienle, et al., "Improved solutions of the steady-state and the time-resolved diffusion equations for reflectance from a semi-infinite turbid medium", J. Opt. Soc. Am. A 14(1), 246 (1997).

Konugolu, et al., "Broadband (600-1350 nm) Time-Resolved Diffuse Optical Spectrometer for Clinical Use", IEEE Journal of Selected Topics in Quantum Electronics, vol. 22, No. 3, May/Jun. 2016.

Lacerenza, et al., "Wearable and wireless time-domain near-infrared spectroscopy system for brain and muscle hemodynamic monitoring", Biomed. Opt. Express 11(10), 5934 (2020).

Lange, et al., "Clinical Brain Monitoring with Time Domain NIRS: A Review and Future Perspectives", Applied Sciences 9(8), 1612 (2019).

Lange, et al., "MAESTROS: A Multiwavelength Time-Domain NIRS System to Monitor Changes in Oxygenation and Oxidation State of Cytochrome-C-Oxidase", IEEE J. Select. Topics Quantum Electron. 25(1), 1-12 (2019).

Martelli, et al., "Optimal estimation reconstruction of the optical properties of a two-layered tissue phantom from time-resolved single-distance measurements", Journal of Biomedical Optics 20(11), 115001 (Nov. 2015).

Mora, et al., "Fast silicon photomultiplier improves signal harvesting and reduces complexity in time-domain diffuse optics", Opt. Express 23(11), 13937 (2015).

(56) References Cited

OTHER PUBLICATIONS

Pifferi, et al., "Performance assessment of photon migration instruments: the MEDPHOT protocol", Applied Optics, 44(11), 2104-2114, 2005.

Prahl, et al., "Optical Absorption of Hemoglobin", http://omlc.ogi.edu/spectra/hemoglobin/index.html, 1999.

Re, et al., "Multi-channel medical device for time domain functional near infrared spectroscopy based on wavelength space multiplexing", Biomed. Opt. Express 4(10), 2231 (2013).

Renna, et al., "Eight-Wavelength, Dual Detection Channel Instrument for Near-Infrared Time-Resolved Diffuse Optical Spectroscopy", IEEE J. Select. Topics Quantum Electron. 25(1), 1-11 (2019).

Torricelli, et al., "Time domain functional NIRS imaging for human brain mapping", NeuroImage 85, 28-50 (2014).

Wabnitz, et al., "Depth-selective data analysis for time-domain fNIRS: moments vs. time windows", Biomed. Opt. Express 11(8), 4224 (2020).

Wabnitz, et al., "Performance assessment of time-domain optical brain imagers, part 1: basic instrumental performance protocol", Journal of Biomedical Optics 19(8), 086010 (Aug. 2014).

Wabnitz, et al., "Performance assessment of time-domain optical brain imagers, part 2: nEUROPt protocol", Journal of Biomedical Optics 19(8), 086012 (Aug. 2014).

Wojtkiewicz, et al., "Self-calibrating time-resolved near infrared spectroscopy", Biomed. Opt. Express 10(5), 2657 (2019).

Zucchelli, et al., "Method for the discrimination of superficial and deep absorption variations by time domain fNIRS", 2013 OSA Dec. 1, 2013 | vol. 4, No. 12 | DOI:10.1364/BOE.4.002893 | Biomedical Optics Express 2893, 2013.

\* cited by examiner

DEVICES, SYSTEMS, AND METHODS FOR CALIBRATING AN OPTICAL MEASUREMENT DEVICE

RELATED APPLICATIONS

The present application claims priority under 35 U.S.C. § 119(e) to U.S. Provisional Patent Application No. 63/226,618, filed Jul. 28, 2021, and incorporated herein by reference in its entirety.

BACKGROUND INFORMATION

A time domain-based optical measurement device (e.g., a near-infrared spectroscopy (TD-NIRS) device) may be configured to perform an optical measurement by emitting picosecond pulses of light into tissue (e.g., brain, muscle, finger, etc.) and detecting arrival times of single photons at nearby detectors. The distribution of photon arrival times may be parameterized to estimate tissue optical properties and/or biological properties (e.g., blood oxygenation levels, blood volume levels, neural activities, etc.).

In some instances, it may be desirable to calibrate the optical measurement device for performing the optical measurement. As an example, the optical measurement device may detect biological properties by measuring the change in shape of laser pulses after they have passed through the tissue. The shape of laser pulses may include a temporal shape, as represented for example by a histogram generated by a time-to-digital converter (TDC) coupled to an output of a detector. To measure the change in the shape, a baseline shape of the laser pulse may be determined to calibrate the optical measurement device. In some scenarios, the baseline shape may change based on various conditions (e.g., temperature, humidity, currents applied to device components, etc.), which may result in a need to periodically calibrate the optical measurement device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

An illustrative system may include a manufactured calibration member configured to support an optical measurement device for performing a calibration operation with respect to the optical measurement device.

For example, the optical measurement device may include a plurality of light sources and a plurality of detectors distributed among a plurality of modules, wherein each module comprises one or more of the light sources and one or more of the detectors. The manufactured calibration member may be made from a material that scatters light. The calibration member may form an exterior surface and may be configured to support the optical measurement device when the optical measurement device is placed on the calibration member. A processing unit may be configured to cause, while the optical measurement device is supported by the calibration member, at least one light source of the plurality of light sources to emit light toward the exterior surface of the calibration member and at least one detector of the plurality of detectors to detect arrival times for photons of the light after the light is scattered by the calibration member, and perform, based on the arrival times, a calibration operation (e.g., determine an instrument response function, a differential nonlinearity, a dark count rate, a time delay associated with the detectors, etc.) with respect to the optical measurement device.

The principles described herein may result in improved calibration of an optical measurement device compared to conventional techniques that do not utilize a manufactured calibration member. For example, the manufactured calibration member may allow a calibration operation with respect to the optical measurement device to be performed more efficiently, consistently, and/or quickly, such as by allowing the calibration operation to be performed concurrently among a plurality of modules of the optical measurement device. This may be beneficial for performing recurring calibrations of the optical measurement device. Moreover, changes in shape of the laser pulses may be more accurately determined than convention techniques, resulting in more accurate determinations of properties of the user, e.g., brain measurement properties of the user. These and other advantages and benefits of the present architectures, systems, and methods are described more fully herein.

Figure 1:
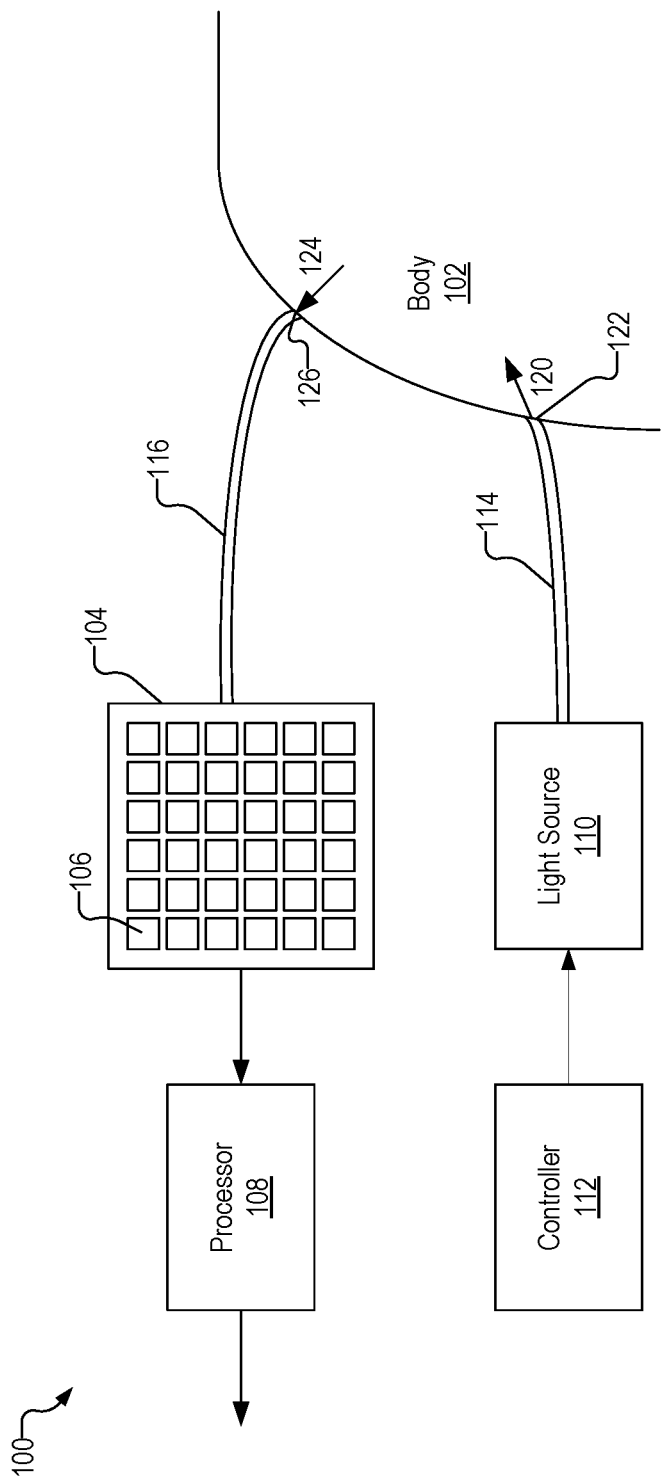
FIG. 1 shows an illustrative optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021 and published as US2021/0259638A1; U.S. patent application Ser. No. 17/176,309, filed Feb. 16, 2021 and published as US2021/0259614A1;

U.S. patent application Ser. No. 17/176,460, filed Feb. 16, 2021 and issued as U.S. Pat. No. 11,096,620; U.S. patent application Ser. No. 17/176,470, filed Feb. 16, 2021 and published as US2021/0259619A1; U.S. patent application Ser. No. 17/176,487, filed Feb. 16, 2021 and published as US2021/0259632A1; U.S. patent application Ser. No. 17/176,539, filed Feb. 16, 2021 and published as US2021/0259620A1; U.S. patent application Ser. No. 17/176,560, filed Feb. 16, 2021 and published as US2021/0259597A1; U.S. patent application Ser. No. 17/176,466, filed Feb. 16, 2021 and published as US2021/0263320A1; Han Y. Ban, et al., "Kernel Flow: A High Channel Count Scalable TD-fNIRS System," SPIE Photonics West Conference (Mar. 6, 2021); and Han Y. Ban, et al., "Kernel Flow: a high channel count scalable time-domain functional near-infrared spectroscopy system," Journal of Biomedical Optics (Jan. 18, 2022), which applications and publications are incorporated herein by reference in their entirety.

In some examples, optical measurement operations performed by optical measurement system 100 are associated with a time domain-based optical measurement technique. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain Digital Optical Tomography (TD-DOT).

Optical measurement system 100 (e.g., an optical measurement system that is implemented by a wearable device or other configuration, and that employs a time domain-based (e.g., TD-NIRS) measurement technique) may detect blood oxygenation levels and/or blood volume levels by measuring the change in shape of laser pulses after they have passed through target tissue, e.g., brain, muscle, finger, etc. As used herein, a shape of laser pulses refers to a temporal shape, as represented for example by a histogram generated by a time-to-digital converter (TDC) coupled to an output of a photodetector, as will be described more fully below.

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as 2" photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diode (m LEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by an arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
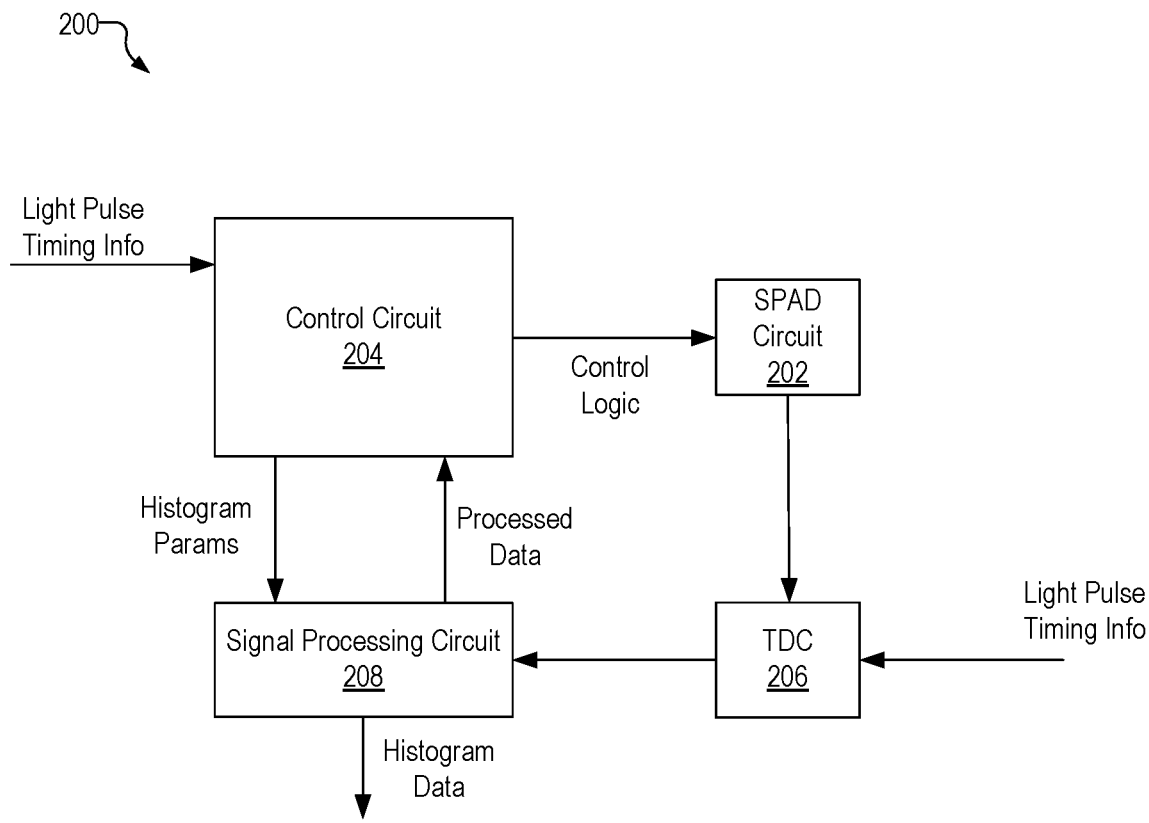
FIG. 2 shows an illustrative detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 may include a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, such as in configurations that implement the systems and methods described herein, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
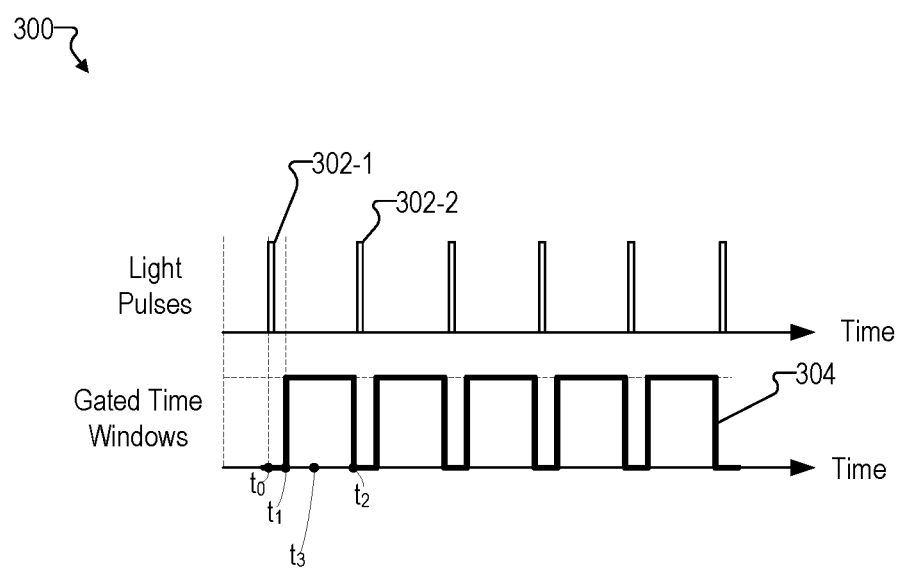
FIG. 3 shows an illustrative timing diagram for performing an optical measurement operation using an optical measurement system.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a finger of a user, tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons.

As shown, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
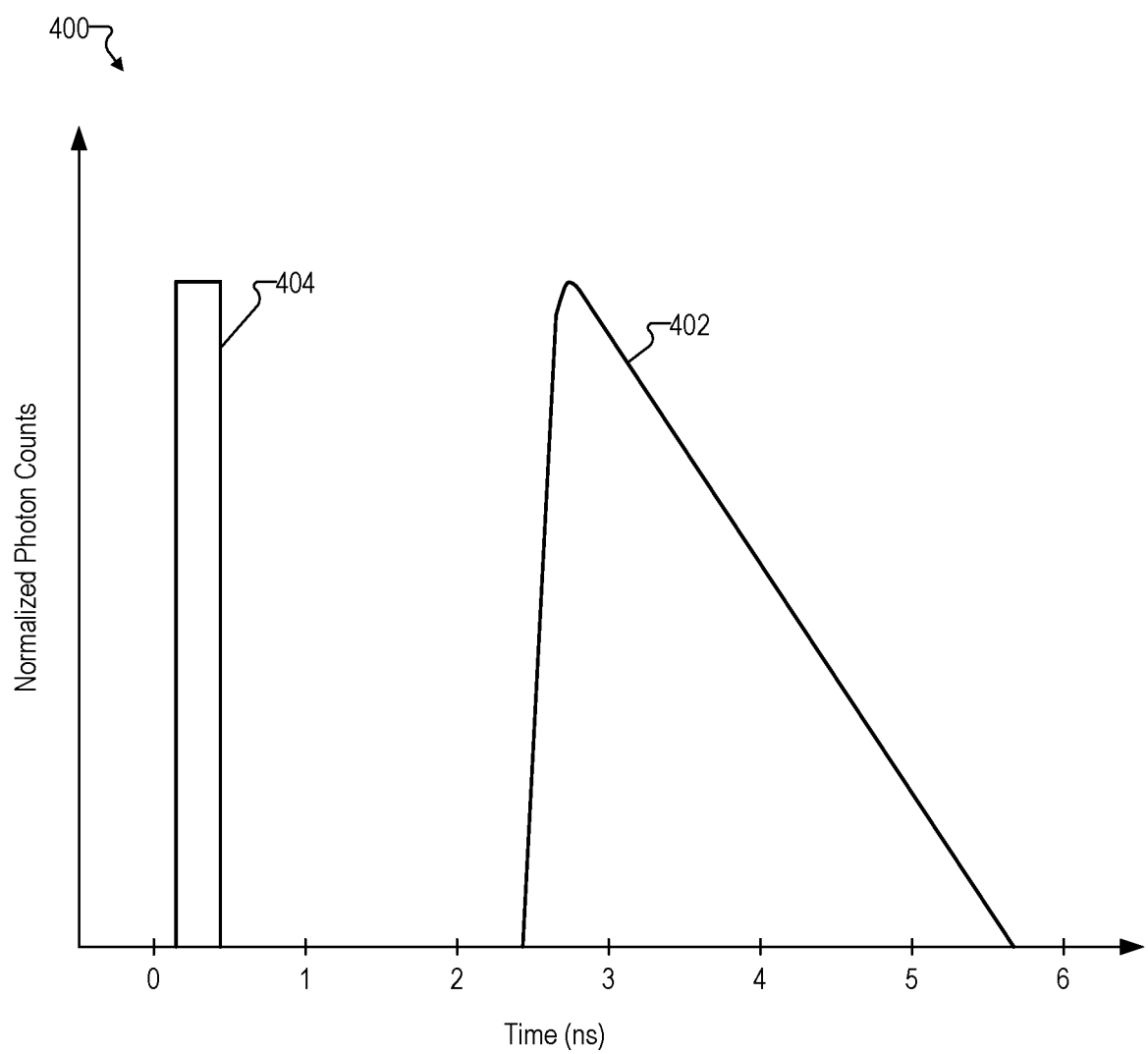
FIG. 4 shows a graph of an illustrative temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological activity, e.g., brain measurement activity from a user.

Optical measurement system 100 may be implemented by or included in any suitable device. For example, optical measurement system 100 may be included in a non-invasive wearable device (e.g., a headpiece) that a user may wear to perform one or more diagnostic, imaging, analytical, and/or consumer-related operations.

Figure 5:
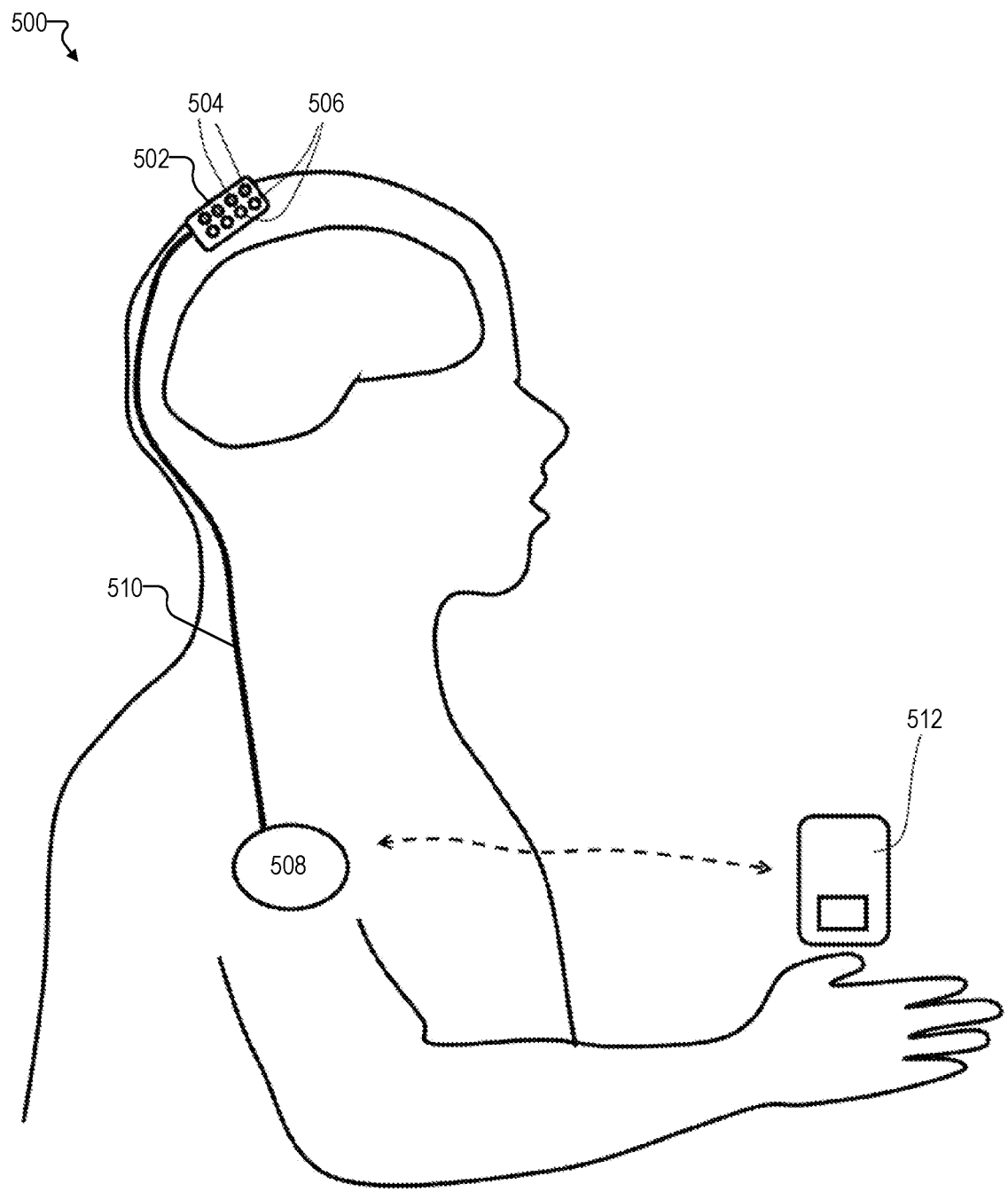
FIG. 5 shows an illustrative non-invasive wearable brain interface system.

To illustrate, FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be a wearable device (e.g., headgear) configured to be worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. For example, other forms conformable to be worn on the user's head include modular assemblies as will described more fully herein. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detectors 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Figure 6A:
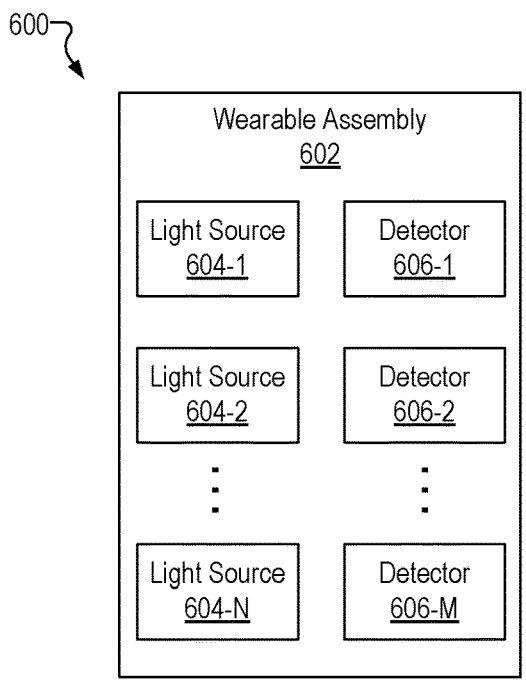
FIG. 6A-6B show an illustrative optical measurement system.
Figure 6B:
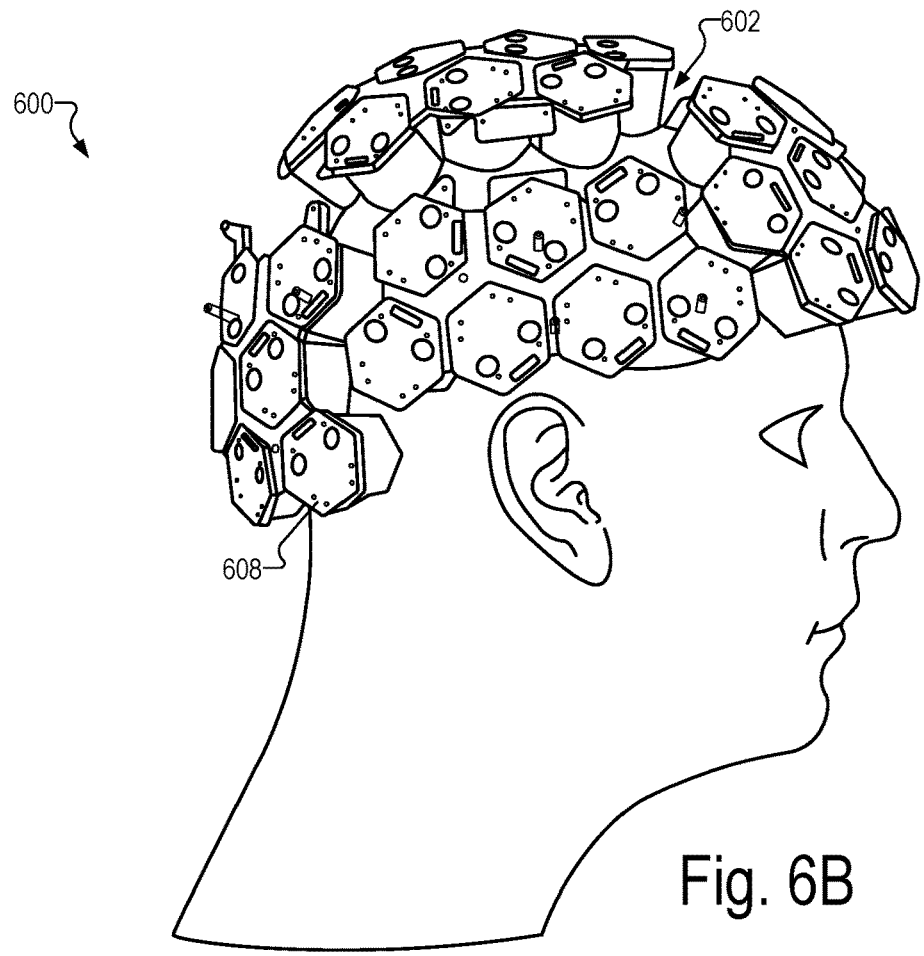

FIGS. 6A-6B shows an exemplary optical measurement system 600 in accordance with the principles described herein. Optical measurement system 600 may be an implementation of optical measurement system 100 and, as shown in FIG. 6A, includes a wearable assembly 602, which includes N light sources 604 (e.g., light sources 604-1 through 604-N) and M detectors 606 (e.g., detectors 606-1 through 606-M). Optical measurement system 600 may include any of the other components of optical measurement system 100 as may serve a particular implementation. N and M may each be any suitable value (i.e., there may be any number of light sources 604 and detectors 606 included in optical measurement system 600 as may serve a particular implementation).

Light sources 604 are each configured to emit light (e.g., a sequence of light pulses) and may be implemented by any of the light sources described herein. Detectors 606 may each be configured to detect arrival times for photons of the light emitted by one or more light sources 604 after the light is scattered by the target. For example, a detector 606 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector).

Wearable assembly 602 may be implemented by any of the wearable devices, modular assemblies, and/or wearable units described herein. For example, as shown in FIG. 6B, wearable assembly 602 may be implemented by a wearable device (e.g., headgear) configured to be worn on a user's head. The TD-NIRS optical measurement system 600 shown in FIG. 6B may include a plurality of modules 608 arranged in a helmet design. Modules 608 may be organized on each side of the head, covering the frontal, parietal, temporal, and occipital cortices. Wearable assembly 602 may additionally or alternatively be configured to be worn on any other part of a user's body.

Optical measurement system 600 may be modular in that one or more components of optical measurement system 600 may be removed, changed out, or otherwise modified as may serve a particular implementation. As such, optical measurement system 600 may be configured to conform to three-dimensional surface geometries, such as a user's head, e.g., see FIG. 6B. Exemplary modular optical measurement systems comprising a plurality of wearable modules are described in more detail in U.S. patent application Ser. No. 17/176,460, filed Feb. 16, 2021 and issued as U.S. Pat. No. 11,096,620, U.S. patent application Ser. No. 17/176,470, filed Feb. 16, 2021 and published as US2021/0259619A1, U.S. patent application Ser. No. 17/176,487, filed Feb. 16, 2021 and published as US2021/0259632A1, U.S. patent application Ser. No. 17/176,539, filed Feb. 16, 2021 and published as US2021/0259620A1, U.S. patent application Ser. No. 17/176,560, filed Feb. 16, 2021 and published as US2021/0259597A1, and U.S. patent application Ser. No. 17/176,466, filed Feb. 16, 2021 and published as US2021/0263320A1, which applications are incorporated herein by reference in their respective entireties.

Figure 7:
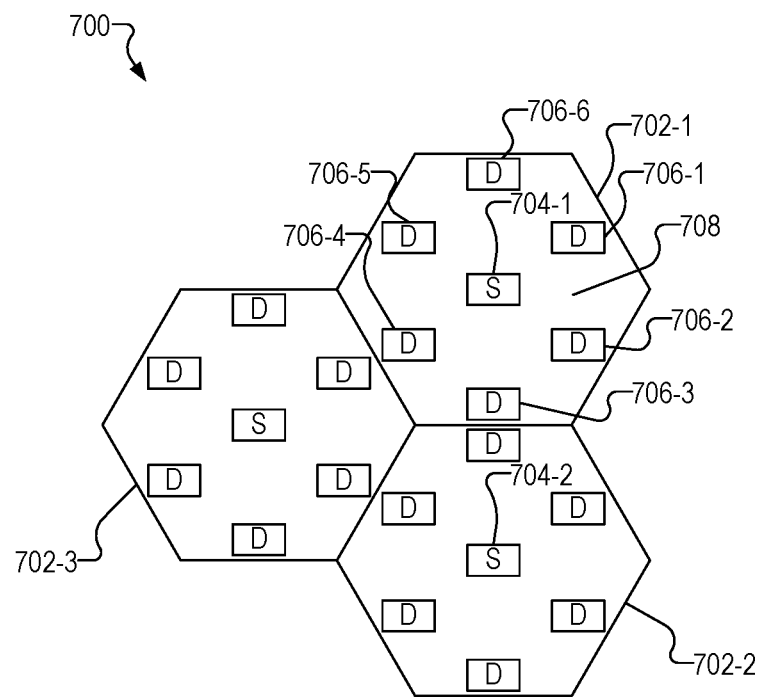
FIG. 7 shows an illustrative modular assembly.

FIG. 7 shows an illustrative modular assembly 700 that may implement optical measurement system 600. Modular assembly 700 is illustrative of the many different implementations of optical measurement system 600 that may be realized in accordance with the principles described herein.

As shown, modular assembly 700 includes a plurality of modules 702 (e.g., modules 702-1 through 702-3). While three modules 702 are shown to be included in modular assembly 700, in alternative configurations, any number of modules 702 (e.g., a single module unit up to sixteen or more module units) may be included in modular assembly 700.

Each module unit 702 includes a light source (e.g., light source 704-1 of module 702-1 and light source 704-2 of module 702-2) and a plurality of detectors (e.g., detectors 706-1 through 706-6 of module 702-1). In the particular implementation shown in FIG. 7, each module unit 702 includes a single light source and six detectors. Each light source is labeled "S" and each detector is labeled "D".

Each light source depicted in FIG. 7 may be implemented by one or more light sources similar to light source 110 and may be configured to emit light directed at a target (e.g., the brain).

Each light source depicted in FIG. 7 may be located at a center region of a surface of the light source's corresponding module. For example, light source 704-1 is located at a center region of a surface 708 of module 702-1. In alternative implementations, a light source of a module may be located away from a center region of the module.

Each detector depicted in FIG. 7 may implement or be similar to detector 104 and may include a plurality of photodetectors (e.g., SPADs) as well as other circuitry (e.g., TDCs), and may be configured to detect arrival times for photons of the light emitted by one or more light sources after the light is scattered by the target.

The detectors of a module may be distributed around the light source of the module. For example, detectors 706 of module 702-1 are distributed around light source 704-1 on surface 708 of module 702-1. In this configuration, detectors 706 may be configured to detect photon arrival times for photons included in light pulses emitted by light source 704-1. In some examples, one or more detectors 706 may be close enough to other light sources to detect photon arrival times for photons included in light pulses emitted by the other light sources. For example, because detector 706-3 is adjacent to module 702-2, detector 706-3 may be configured to detect photon arrival times for photons included in light pulses emitted by light source 704-2 (in addition to detecting photon arrival times for photons included in light pulses emitted by light source 704-1).

In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling) information about the detected signals. Detectors of a module may be alternatively disposed on the module as may serve a particular implementation.

Figure 8A:
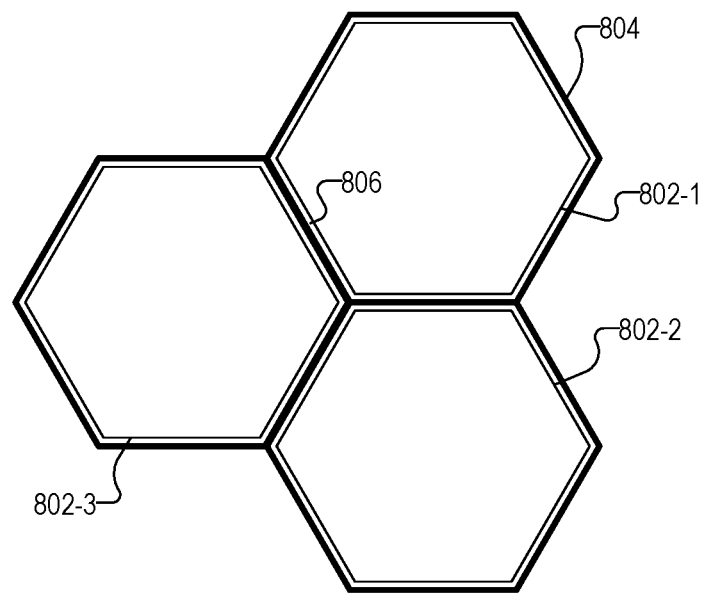
FIGS. 8A-8B show an illustrative implementation of the modular assembly of FIG. 7.
Figure 8B:
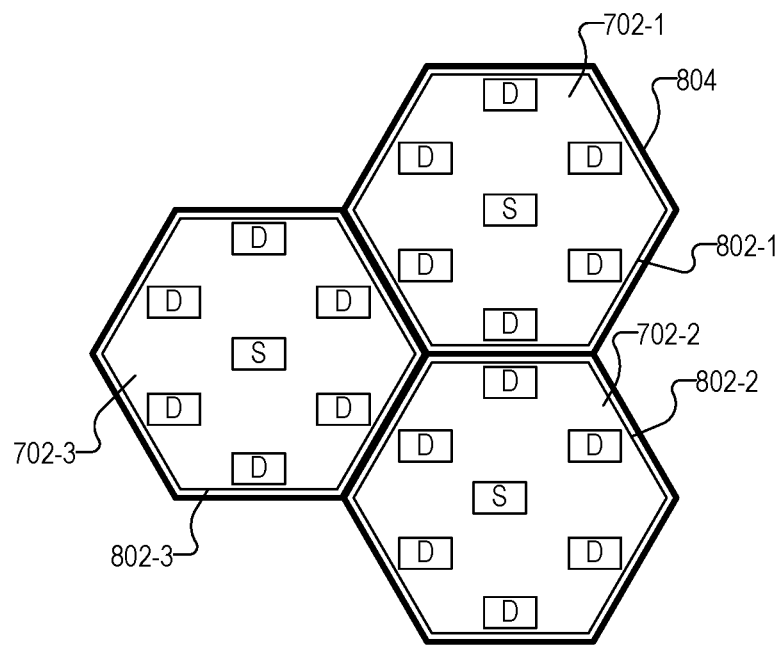

In FIG. 7, modules 702 are shown to be adjacent to and touching one another. Modules 702 may alternatively be spaced apart from one another. For example, FIGS. 8A-8B show an exemplary implementation of modular assembly 700 in which modules 702 are configured to be inserted into individual slots 802 (e.g., slots 802-1 through 802-3, also referred to as cutouts) of a wearable assembly 804. In particular, FIG. 8A shows the individual slots 802 of the wearable assembly 804 before modules 702 have been inserted into respective slots 802, and FIG. 8B shows wearable assembly 804 with individual modules 702 inserted into respective individual slots 802.

Wearable assembly 804 may implement wearable assembly 602 and may be configured as headgear and/or any other type of device configured to be worn by a user.

As shown in FIG. 8A, each slot 802 is surrounded by a wall (e.g., wall 806) such that when modules 702 are inserted into their respective individual slots 802, the walls physically separate modules 702 one from another. In alternative embodiments, a module (e.g., module 702-1) may be in at least partial physical contact with a neighboring module (e.g., module 702-2).

Each of the modules described herein may be inserted into appropriately shaped slots or cutouts of a wearable assembly, as described in connection with FIGS. 8A-8B.

As shown in FIGS. 7 and 8B, modules 702 may have a hexagonal shape. Modules 702 may alternatively have any other suitable geometry (e.g., in the shape of a pentagon, octagon, square, rectangular, circular, triangular, free-form, etc.).

In some examples, any of the optical measurement systems described herein may be implemented by a wearable multimodal measurement system configured to perform both optical-based brain data acquisition operations and electrical-based brain data acquisition operations, such as any of the wearable multimodal measurement systems described in U.S. Patent Application Publication Nos. 2021/0259638 and 2021/0259614, which publications are incorporated herein by reference in their respective entireties.

Figure 9:
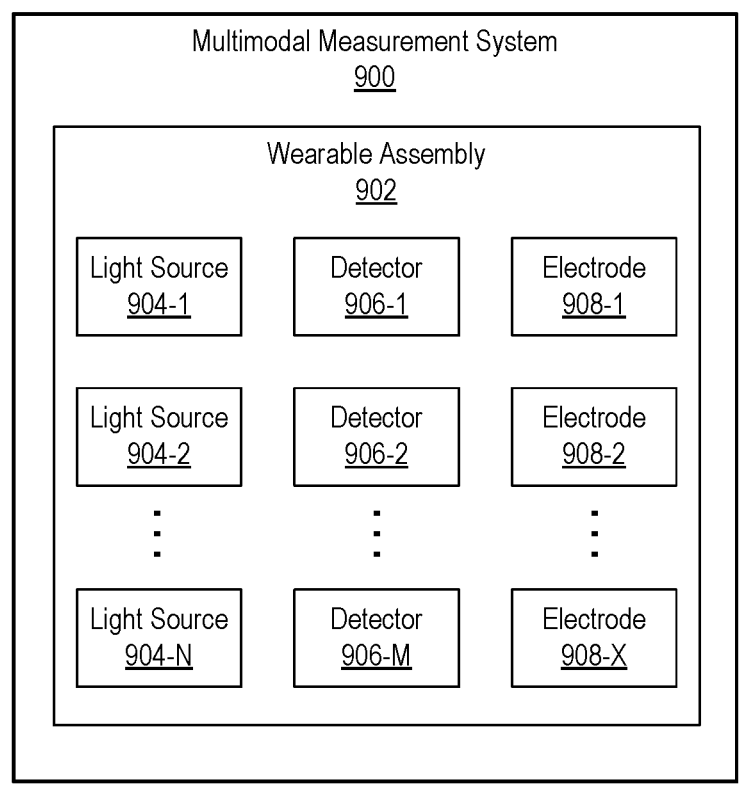
FIG. 9 shows an illustrative multimodal measurement system.
Figure 10:
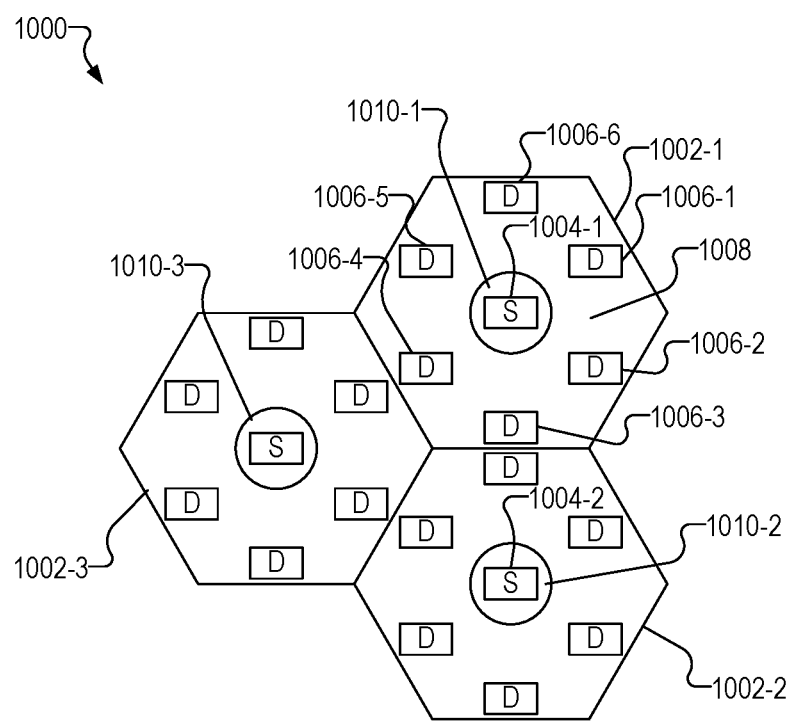
FIG. 10 shows an illustrative modular assembly.

To illustrate, FIGS. 9-10 show various multimodal measurement systems that may implement optical measurement system 100. The multimodal measurement systems described herein are merely illustrative of the many different multimodal-based brain interface systems that may be used in accordance with the systems and methods described herein.

FIG. 9 shows an exemplary multimodal measurement system 900 in accordance with the principles described herein. Multimodal measurement system 900 may at least partially implement optical measurement system 100 and, as shown, includes a wearable assembly 902 (which may be similar to wearable assembly 602), which includes N light sources 904 (e.g., light sources 904-1 through 904-N, which are similar to light sources 604), M detectors 906 (e.g., detectors 906-1 through 906-M, which are similar to detectors 606), and X electrodes (e.g., electrodes 908-1 through 908-X). Multimodal measurement system 900 may include any of the other components of optical measurement system 100 as may serve a particular implementation. N, M, and X may each be any suitable value (i.e., there may be any number of light sources 904, any number of detectors 906, and any number of electrodes 908 included in multimodal measurement system 900 as may serve a particular implementation).

Electrodes 908 may be configured to detect electrical activity within a target (e.g., the brain). Such electrical activity may include electroencephalogram (EEG) activity and/or any other suitable type of electrical activity as may serve a particular implementation. In some examples, electrodes 908 are all conductively coupled to one another to create a single channel that may be used to detect electrical activity. Alternatively, at least one electrode included in electrodes 908 is conductively isolated from a remaining number of electrodes included in electrodes 908 to create at least two channels that may be used to detect electrical activity.

FIG. 10 shows an illustrative modular assembly 1000 that may implement multimodal measurement system 900. As shown, modular assembly 1000 includes a plurality of modules 1002 (e.g., modules 1002-1 through 1002-3). While three modules 1002 are shown to be included in modular assembly 1000, in alternative configurations, any number of modules 1002 (e.g., a single module up to sixteen or more modules) may be included in modular assembly 1000. Moreover, while each module 1002 has a hexagonal shape, modules 1002 may alternatively have any other suitable geometry (e.g., in the shape of a pentagon, octagon, square, rectangular, circular, triangular, free-form, etc.).

Each module 1002 includes a light source (e.g., light source 1004-1 of module 1002-1 and light source 1004-2 of module 1002-2) and a plurality of detectors (e.g., detectors 1006-1 through 1006-6 of module 1002-1). In the particular implementation shown in FIG. 10, each module 1002 includes a single light source and six detectors. Alternatively, each module 1002 may have any other number of light sources (e.g., two light sources) and any other number of detectors. The various components of modular assembly 1000 shown in FIG. 10 are similar to those described in connection with FIG. 7.

As shown, modular assembly 1000 further includes a plurality of electrodes 1010 (e.g., electrodes 1010-1 through 1010-3), which may implement electrodes 908. Electrodes 1010 may be located at any suitable location that allows electrodes 1010 to be in physical contact with a surface (e.g., the scalp and/or skin) of a body of a user. For example, in modular assembly 1000, each electrode 1010 is on a module surface configured to face a surface of a user's body when modular assembly 1000 is worn by the user. To illustrate, electrode 1010-1 is on surface 1008 of module 1002-1. Moreover, in modular assembly 1000, electrodes 1010 are located in a center region of each module 1002 and surround each module's light source 1004. Alternative locations and configurations for electrodes 1010 are possible.

Figure 11:
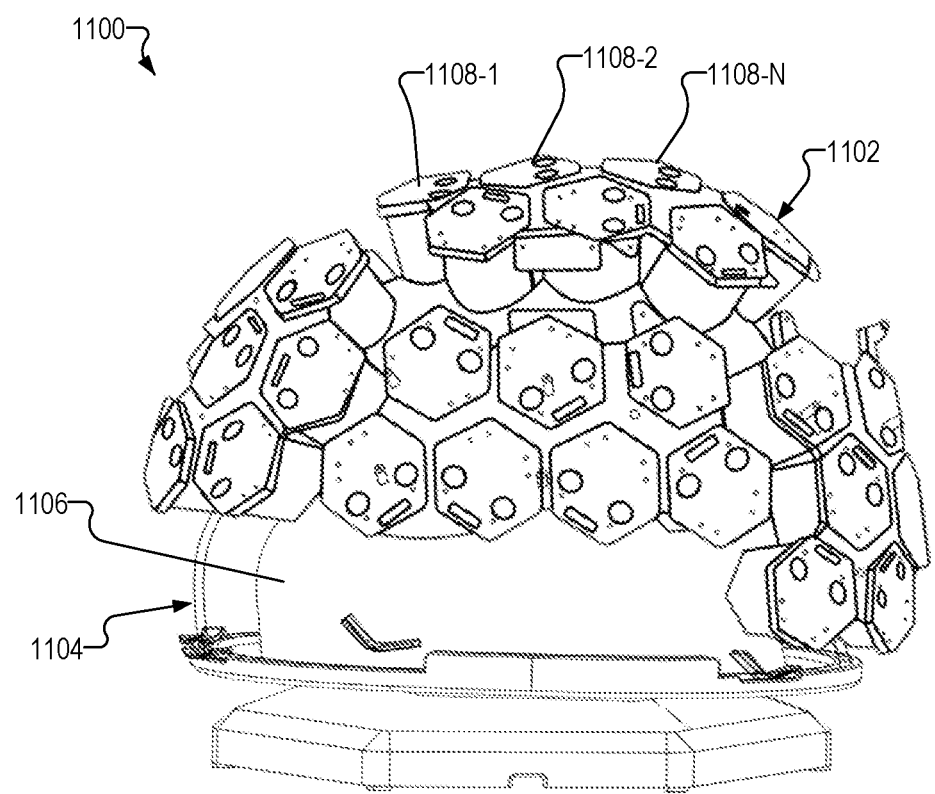
FIG. 11 shows an illustrative calibration system.

FIG. 11 shows an illustrative implementation 1100 of a system that may be used to perform a calibration operation with respect to an optical measurement device 1102. As shown, implementation 1100 includes a calibration assembly 1104 having a calibration member 1106 configured to support optical measurement device 1102. Implementation 1100 may include additional or alternative components as may serve a particular implementation.

Optical measurement device 1102 is illustrative of the many different implementations of optical measurement system 600 that may be realized in accordance with the principles described herein. As shown, optical measurement device 1102 includes a plurality of modules 1108 (e.g., modules 1108-1 through 1108-N, where N may be any suitable value as may serve a particular implementation) having a plurality of light sources and a plurality of detectors distributed among the plurality of modules 1108. Each light source of optical measurement device 1102 may be implemented by one or more light sources similar to light source 604 and may be configured to emit light directed at a target (e.g., the brain, calibration member 1106, etc.). Each detector of optical measurement device 1102 may implement or be similar to detector 606 and may include a plurality of photodetectors (e.g., SPADs) as well as other circuitry (e.g., TDCs), and may be configured to detect arrival times for photons of the light emitted by one or more light sources after the light is scattered by the target. Each module 1108 of optical measurement device 1102 may implement or be similar to module 608 and may be arranged in a wearable assembly (e.g., wearable assembly 602) that may be implemented by any of the wearable devices, modular assemblies, and/or wearable units described herein.

Figure 12A:
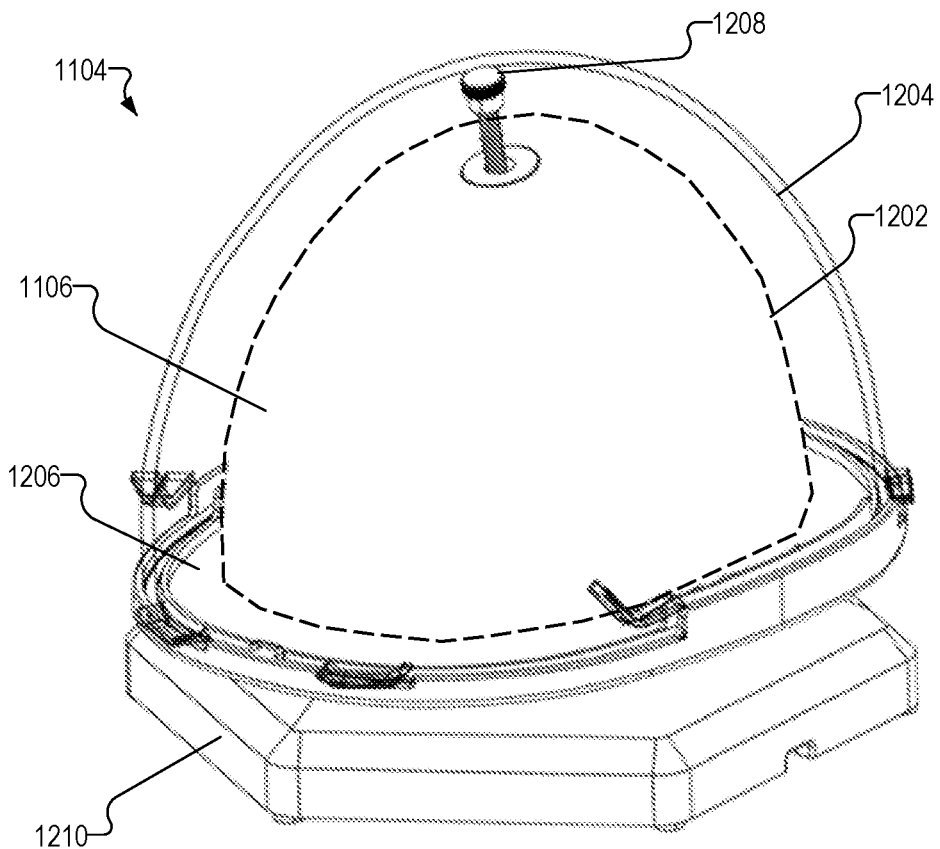
FIG. 12A shows a calibration assembly of the calibration system of FIG. 11.
Figure 12B:
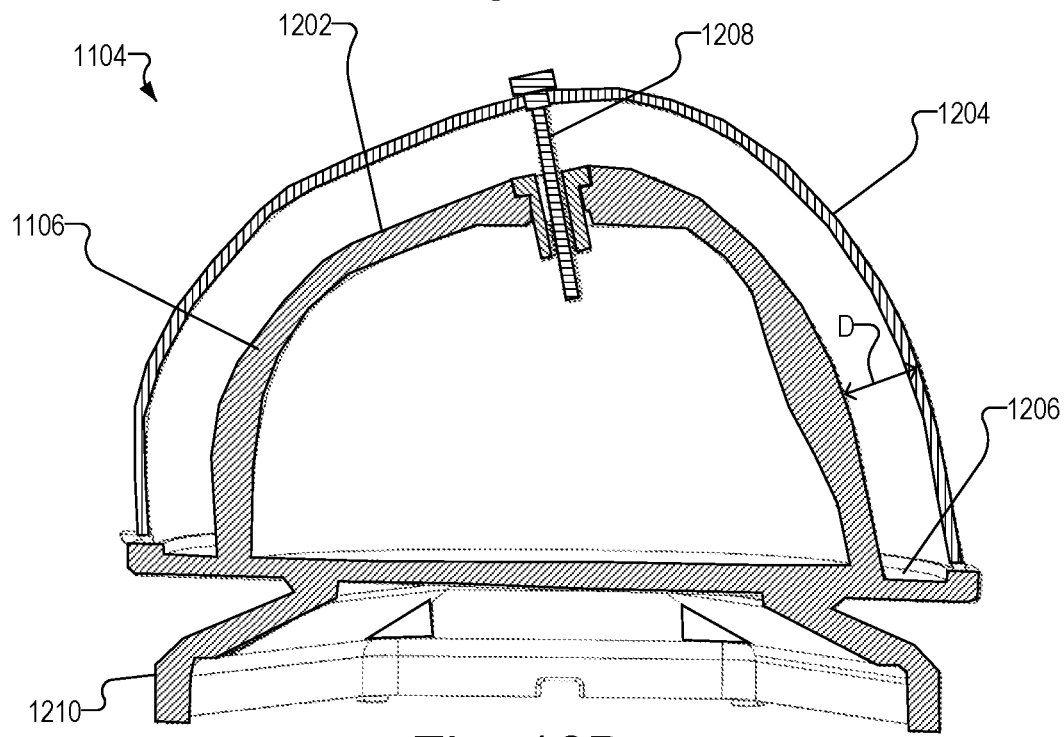
FIG. 12B shows a cross-sectional view of the calibration assembly of FIG. 12A.

FIGS. 12A and 12B show calibration assembly 1104 of implementation 1100 in more detail. As shown, calibration assembly 1104 includes calibration member 1106 forming an exterior surface 1202 and a shell 1204 positioned about exterior surface 1202. Exterior surface 1202 may be formed in a generally arcuate dome-shaped configuration. For example, exterior surface 1202 may include a head-shaped geometry that corresponds to an interior surface of optical measurement device 1102. In some implementations, exterior surface 1202 may include one or more flattened areas that may form a plane substantially parallel to a module 1108 of optical measurement device 1102 aligned with the flattened area. Still other suitable geometries for exterior surface 1202 of calibration member 1106 may be used to support optical measurement device 1102.

Calibration member 1106 may be manufactured (e.g., 3D printed, injection molded, or otherwise manufactured) from a material that scatters light. For example, calibration member 1106 may be made from a light-absorbing material (e.g., an opaque material) configured to absorb a first subset of photons of the light emitted by at least one light source of optical measurement device 1102 and reflect a second subset of photons of the light emitted by at least one light source of optical measurement device 1102. In some implementations, calibration member 1106 may be made from a highly absorbing material (e.g., a black and/or dark material) such that the first subset of photons absorbed by calibration member 1106 is greater than the second subset of photons reflected by calibration member 1106. Alternatively, calibration member 1106 may be made from a translucent material that diffuses light within calibration member 1106. In some implementations, calibration member 1106 may be formed by the material that scatters light and/or the material that scatters light may be applied to exterior surface 1202 of calibration member 1106 as a finish (e.g., a paint or other applied finish). Exterior surface 1202 of calibration member 1106 may include any suitable finish (e.g., matte, glossy, smooth, textured, etc.).

In some implementations, a shell 1204 may be positioned between optical measurement device 1102 and calibration member 1106 to further support optical measurement device 1102 on calibration member 1106. Shell 1204 may be made from a translucent material configured to allow light to pass therethrough. As shown, shell 1204 may include an arcuate dome-shaped configuration that corresponds to the interior surface of optical measurement device 1102 and/or exterior surface 1202 of calibration member 1106. This may allow the exterior surface of shell 1204 to receive the interior surface of optical measurement device 1102.

An interior surface of shell 1204 may be placed directly on exterior surface 1202 of calibration member 1106 and/or the interior surface of shell 1204 may be spaced from exterior surface 1202, as shown in FIGS. 12A and 12B. For example, calibration member 1106 may include an annular flange 1206 extending outwardly about a circumference of calibration member 1106 that is configured to receive shell 1204 in order to space shell 1204 from exterior surface 1202 of calibration member 1106. Shell 1204 may thereby be configured to space optical measurement device 1102 at a uniform distance D away from exterior surface 1202 of calibration member 1106. Alternatively, shell 1204 may be omitted such that the interior surface of optical measurement device 1102 may be placed directly on exterior surface 1202 of calibration member 1106. Calibration member 1106 may further be used to store optical measurement device 1102 while optical measurement device 1102 is not in use.

In some implementations, shell 1204 may rest (e.g., due to gravity) on calibration member 1106 and/or shell 1204 may be selectively coupled with calibration member 1106. For example, shell 1204 and/or calibration member 1106 may include one or more openings configured to receive a fastener 1208 (e.g., a bolt, a screw, a pin, etc.) to selectively couple shell 1204 with calibration member 1106. Still other suitable configurations for coupling shell 1204 with calibration member 1106 may be used. For example, shell 1204 may be integrally formed and/or otherwise coupled with calibration member 1106 (e.g., by adhesive, welding, friction fit, etc.).

In some implementations, calibration assembly 1104 may further include a base 1210 attached with calibration member 1106 and configured to support calibration member 1106. For example, base 1210 may extend outwardly from a bottom portion of calibration member 1106 to allow calibration member 1106 to be placed on a table or other surface. Base 1210 may be integrally formed and/or otherwise coupled with calibration member 1106 (e.g., by fasteners, adhesive, welding, friction fit, etc.).

Figure 13:
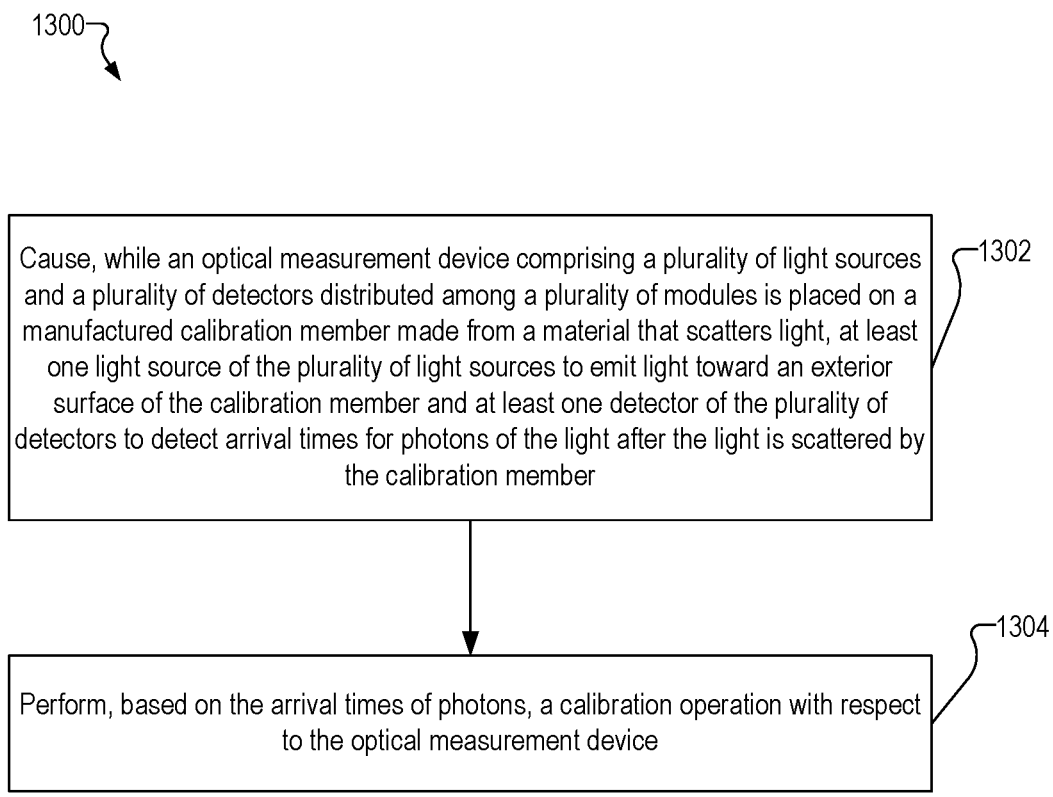
FIG. 13 shows an illustrative method for performing a calibration operation.

FIG. 13 shows an illustrative method 1300 for performing a calibration operation with respect to optical measurement device 1102. While FIG. 13 illustrates exemplary operations according to one embodiment, other embodiments may omit, add to, reorder, and/or modify any of the operations shown in FIG. 13. Moreover, each of the operations depicted in FIG. 13 may be performed in any of the ways described herein. In some implementations, method 1300 may be implemented by one or more computing devices (e.g., processor 108) that may be coupled (e.g., wired and/or wirelessly) with optical measurement device 1102.

As shown, method 1300 may, at operation 1302, include causing, while optical measurement device 1102 comprising a plurality of light sources and a plurality of detectors distributed among a plurality of modules 1108 is placed on a manufactured calibration member 1106 made from a material that scatters light, at least one light source of the plurality of light sources to emit light toward exterior surface 1202 of calibration member 1106 and at least one detector of the plurality of detectors to detect arrival times for photons of the light after the light is scattered by calibration member 1106. Method 1300 may, at operation 1304, further include performing, based on the arrival times of photons, a calibration operation with respect to optical measurement device 1102.

In some implementations, the calibration operation may include adjusting a time delay associated with the detectors of optical measurement device 1102. The time delay may be adjusted in any suitable manner. For example, an offset may, in some instances, exist between a mean of the arrival times of photons detected between two or more detectors within each module 1108 and/or between two or more modules 1108. In such instances, the offset may be adjusted such that the mean arrival times of photons detected by two or more detectors is substantially similar.

Additionally or alternatively, the calibration operation may include determining, with respect to optical measurement device 1102, an instrument response function (IRF). The IRF may be determined in any suitable manner. As an illustrative example, the IRF may represent a baseline shape of the light pulse emitted from a light source of optical measurement device 1102. An initial value for the IRF may be based on a measured IRF, where light pulses may be directed from a light source of optical measurement device 1102 directly toward calibration member 1106, which is made from material having known optical properties (e.g., absorption, reflection, etc.). By counting the number of photons detected at each time relative to each light pulse repeated over a plurality of light pulses, the system of implementation 1100 may generate a histogram that represents a light pulse response of calibration member 1106 (e.g., a temporal point spread function (TPSF)) and designate the histogram as the IRF.

In some implementations, the calibration operation may include filtering photons that undergo multiple reflections from calibration member 1106. For example, expected time of flight characteristics for photons traveling from a light source of optical measurement device 1102, reflecting off calibration member 1106, and reaching a detector of optical measurement device 1102 may be determined based on the known optical properties of calibration member 1106 and the uniform distance D between optical measurement device 1102 and calibration member 1106. The expected time of flight characteristics may be used to filter photons that undergo multiple reflections from calibration member 1106, which may avoid muti-path errors from distorting the calibration operation.

The calibration operation may be performed with respect to a single module 1108 and/or among two or more modules 1108. For example, performing the calibration operation may be based on emitting light from at least one light source of a first module (e.g., 1108-1) toward exterior surface 1202 of calibration member 1106 and detecting, by at least one detector of a second module (e.g., 1108-2), arrival times for photons of the light after the light is scattered by calibration member 1106.

The calibration operation may be performed at any desired interval (e.g., when optical measurement device 1102 is powered on, between measurements of a user performed by optical measurement device 1102, between users of optical measurement device 1102, when optical measurement device 1102 reaches an operating temperature, etc.). In some implementations, the processor (e.g., processor 108) may cause the calibration operation to be performed automatically at the desired interval. During the calibration operation, one or more light sources of optical measurement device 1102 may be actuated simultaneously and/or sequentially to perform the calibration operation. In some implementations, actuation of the light sources may be optimized to perform the calibration operation. For example, multiple light sources may be actuated in a pattern such that each detector may only detect light emitted from one light source at a time. Still other suitable methods for performing the calibration operation with calibration member 1106 may be used.

Figure 14:
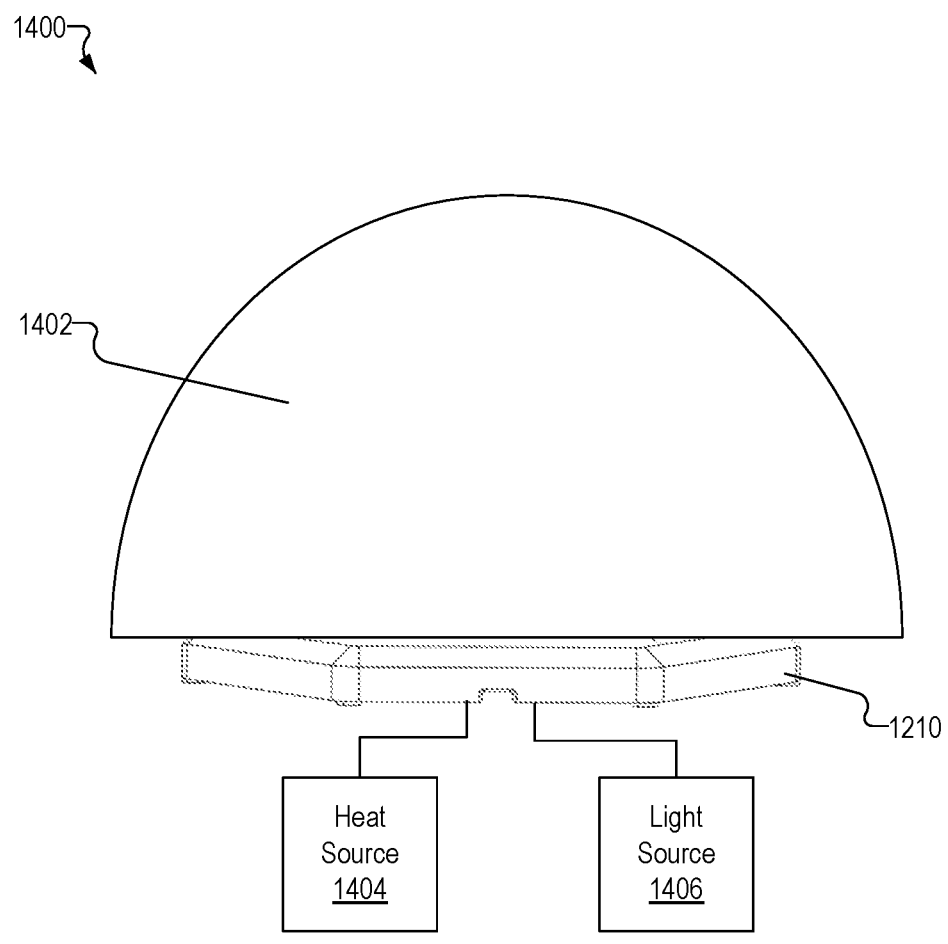
FIG. 14 shows an illustrate calibration system.

FIG. 14 shows another illustrative implementation 1400 of a system that may be used to perform a calibration operation with respect to an optical measurement device 1102. Implementation 1400 may implement or be similar to implementation 1100 and, as shown, further includes a cover 1402, a heat source 1404, and a light source 1406. Implementation 1400 may include additional or alternative components as may serve a particular implementation.

Cover 1402 may be configured to cover optical measurement device 1102 while optical measurement device 1102 is positioned on calibration member 1106. Accordingly, cover 1402 may, while the system is not in use, be configured to store optical measurement device 1102 and/or calibration member 1106 to protect optical measurement device 1102 and/or calibration member 1106 from dust or debris. In some implementations, cover 1402 may be used for performing the calibration operation with respect to optical measurement device 1102. For example, the calibration operation may include determining a dark count rate associated with the detectors of optical measurement device 1102, which may be performed in any suitable manner. In these instances, cover 1402 may be made from an opaque material and may be positioned over optical measurement device 1102 to inhibit light from entering optical measurement device 1102.

Heat source 1404 may be implemented by any suitable heating device and may be configured to heat optical measurement device 1102 and/or calibration member 1106 such as for performing the calibration operation. Heat source 1404 may be included in calibration assembly 1104 and/or as a separate device coupled with calibration assembly 1104 and/or optical measurement device 1102. Heat source 1404 may allow the calibration operation to be performed more quickly and/or accurately. For example, heat source 1404 may decrease the amount of time for heating optical measurement device 1102 to reach an operating temperature and allow the calibration operation to be performed at the operating temperature. In some implementations, cover 1402 may be used in combination with heat source 1404 such that cover 1402 may insulate optical measurement device 1102 during heating by heat source 1404 and allow optical measurement device 1102 to reach the operating temperature more quickly. In some implementations, optical measurement device 1102 may include a temperature sensor configured to measure a temperature of optical measurement device 1102 such that operation of heat source 1404 may be based on the temperature of optical measurement device 1102.

Light source 1406 may be implemented by any suitable light source (e.g., a continuous wave light source) and configured to emit light toward at least one detector of the plurality of detectors of optical measurement device 1102. Light source 1406 may be included in calibration assembly 1104 and/or as a separate device coupled with calibration assembly 1104 and/or optical measurement device 1102. In some implementations, light source 1406 may be used to perform the calibration operation with respect to optical measurement device 1102. For example, light source 1406 may be used to perform a differential nonlinearity measurement, in any suitable manner, with respect to optical measurement device 1102.

Figure 15A:
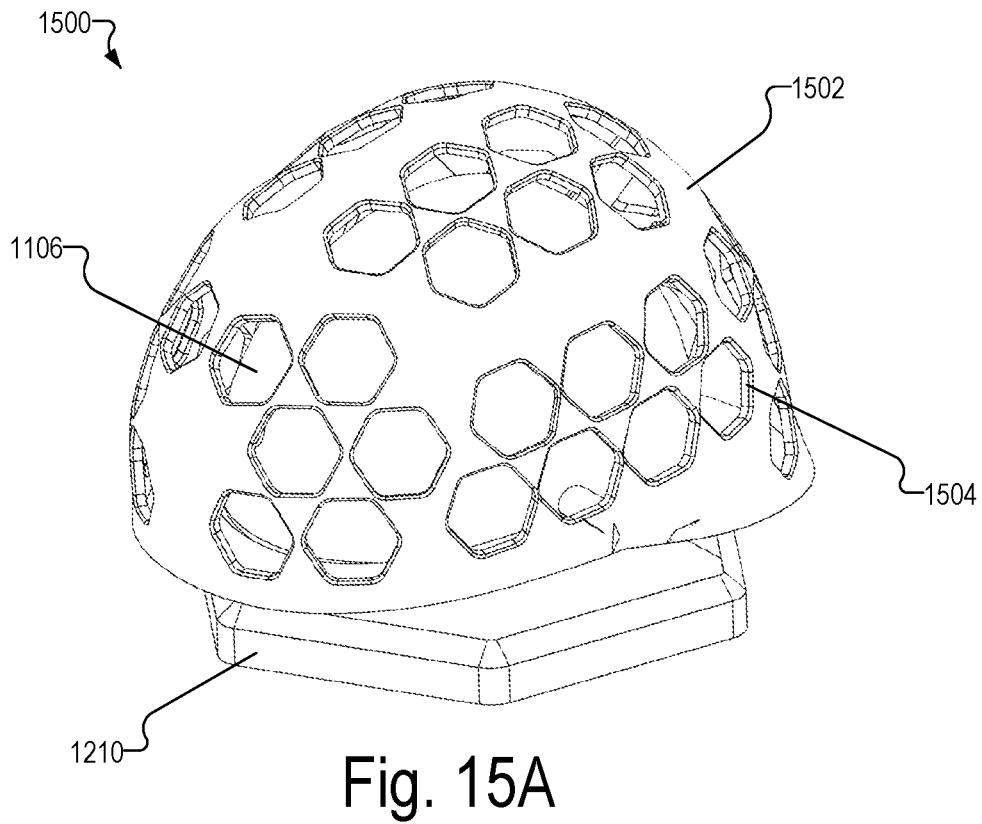
FIG. 15A shows an illustrative calibration assembly.
Figure 15B:
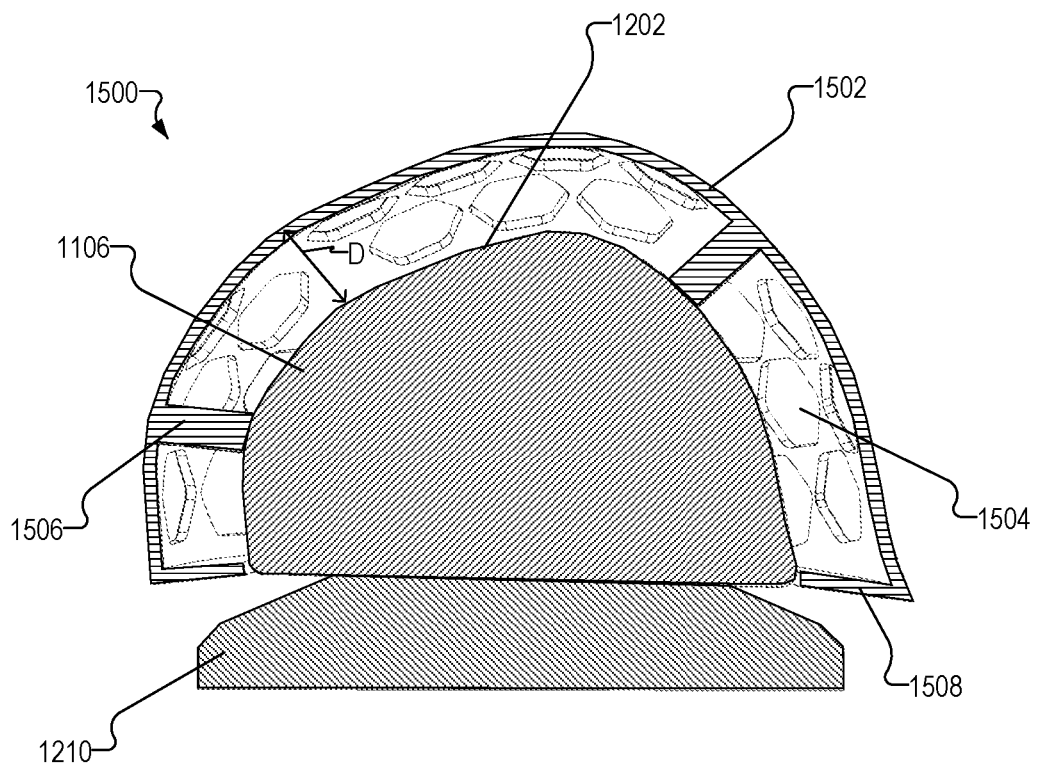
FIG. 15B shows a cross-sectional view of the calibration assembly of FIG. 15A.

FIGS. 15A and 15B show an illustrative implementation 1500 of a calibration assembly that may be used to perform a calibration operation with respect to an optical measurement device 1102. As shown, implementation 1500 may implement or be similar to calibration assembly 1104 except that implementation 1500 includes a frame 1502 positioned between optical measurement device 1102 and calibration member 1106 instead of a shell 1204. Implementation 1500 may include additional or alternative components as may serve a particular implementation.

As shown, frame 1502 forms one or more openings 1504 extending through frame 1502. Each opening 1504 may be configured to receive, while frame 1502 is positioned on calibration member 1106, a module 1108 of optical measurement device 1102 therethrough to support optical measurement device 1102 on calibration member 1106. Frame 1502 may form an arcuate dome-shaped configuration that corresponds to the interior surface of optical measurement device 1102 and/or exterior surface 1202 of calibration member 1106. An interior surface of frame 1502 may be spaced from exterior surface 1202 of calibration member 1106, as shown in FIGS. 15A and 15B.

For example, frame 1502 may include one or more support members 1506 extending inwardly from one or more portions within frame 1502 and/or an annular flange 1508 extending inwardly about a circumference of frame 1502, which may be configured to abut exterior surface 1202 of calibration member 1106 to space frame 1502 from exterior surface 1202 of calibration member 1106. Frame 1502 may thereby be configured to space optical measurement device 1102 a uniform distance D away from exterior surface 1202 of calibration member 1106 while optical measurement device 1102 is positioned on frame 1502. In some implementations, frame 1502 may be configured to rest (e.g., by gravity) on calibration member 1106 and/or be selectively coupled with calibration member 1106. For example, frame 1502 may be integrally formed and/or otherwise coupled with calibration member 1106 (e.g., by fasteners, adhesive, welding, friction fit, etc.).

Figure 16A:
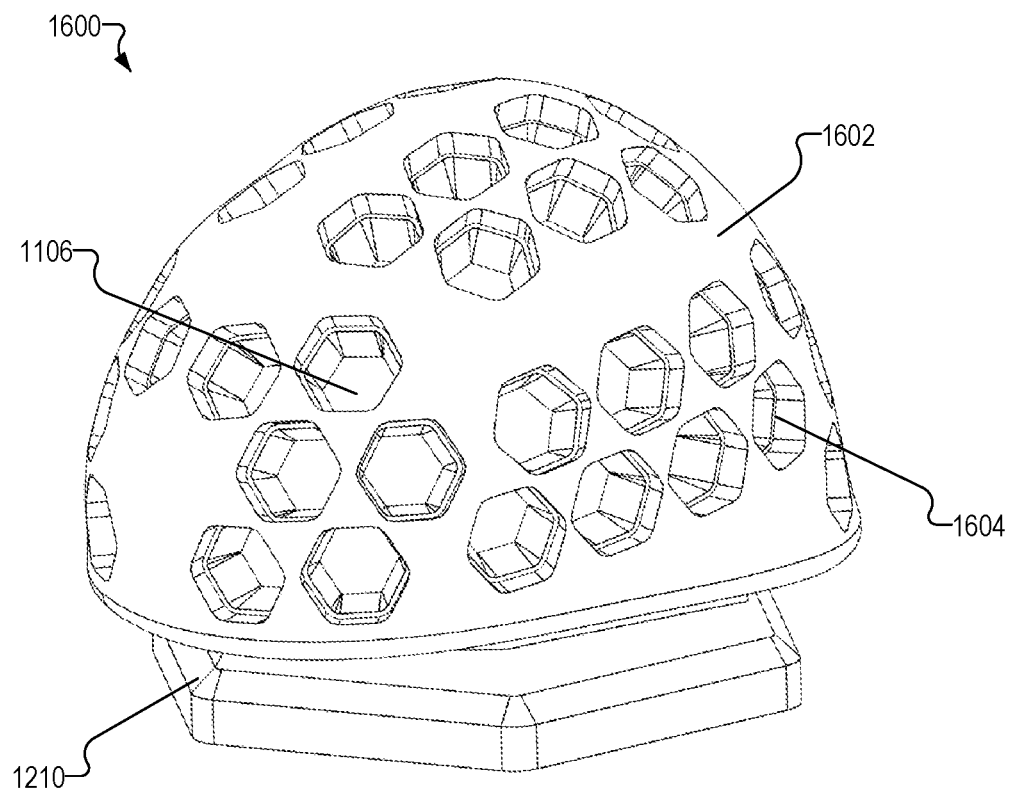
FIG. 16A shows an illustrative calibration assembly.
Figure 16B:
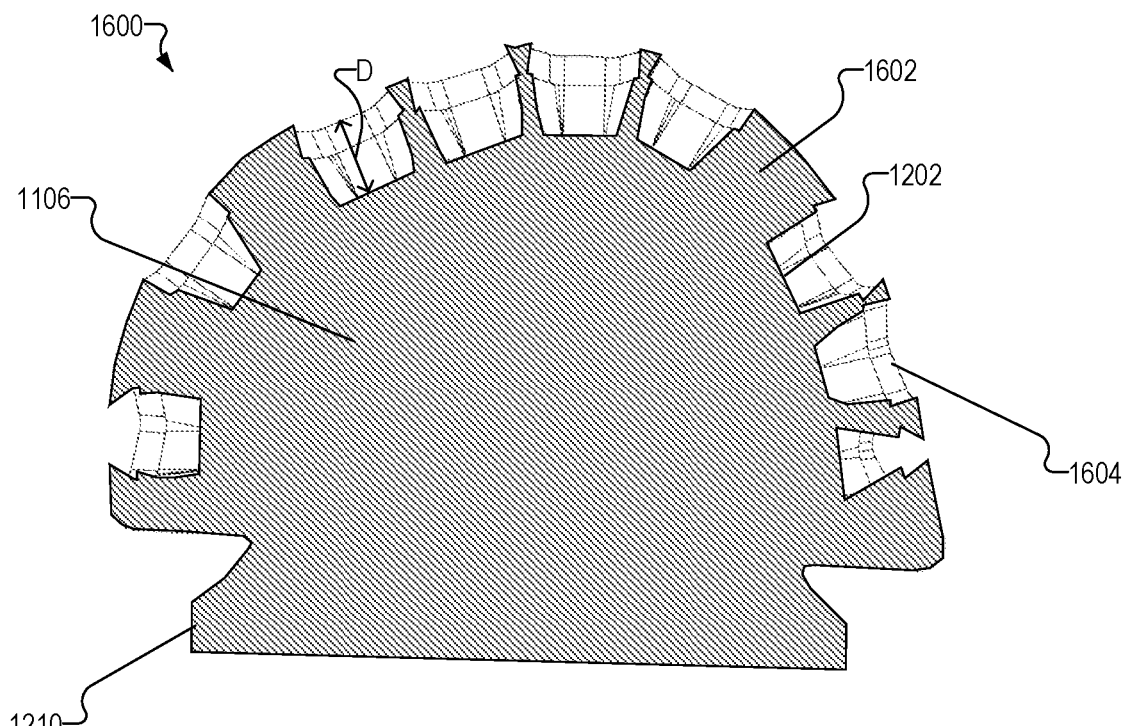
FIG. 16B shows a cross-sectional view of the calibration assembly of FIG. 16A.

FIGS. 16A and 16B show an illustrative implementation 1600 of a calibration assembly that may be used to perform a calibration operation with respect to an optical measurement device 1102. Implementation 1600 may implement or be similar to implementation 1500, except that a frame 1602 of implementation 1600 may be integrally formed with calibration member 1106. For example, frame 1602 may form a plurality of openings 1604 extending through frame 1602 to exterior surface 1202 of calibration member 1106. Openings 1604 may be configured to receive a module 1108 of optical measurement device 1102. In some implementations, openings 1604 may extend at varying depths within frame 1602 and/or extend at substantially similar depths to position each module 1108 of optical measurement device 1102 at a uniform distance D from exterior surface 1202 of calibration member 1106. Implementation 1600 may include additional or alternative components as may serve a particular implementation.

Figure 17:
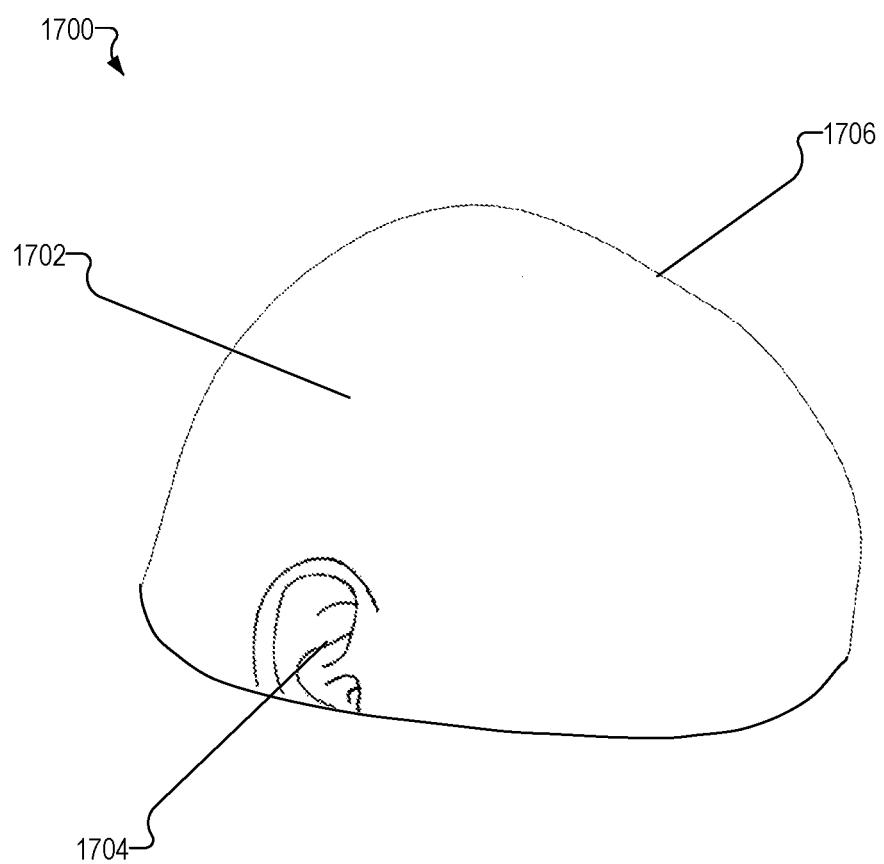
FIG. 17 shows an illustrative calibration member.

FIG. 17 shows an illustrative implementation 1700 of a calibration member 1702 that may be used to perform a calibration operation with respect to an optical measurement device 1102. Calibration member 1702 may implement or be similar to calibration member 1106 and, as shown, further includes one or more anatomical features 1704 positioned on an exterior surface 1706 of calibration member 1702. In the illustrated version, anatomical feature 1704 includes an ear extending from exterior surface 1706, though other suitable anatomical features may be used. For example, other anatomical features may be used, such as anatomical features associated with a head (e.g., eyes, nose, mouth, etc.) and/or other parts of the body. This may allow calibration member 1702 to appear more realistic. In some implementations, anatomical feature 1704 may be used for performing the calibration operation. For example, anatomical feature 1704 may be used to reflect light emitted from optical measurement device 1102 similar to a target feature.

An illustrative system may include an optical measurement device comprising a plurality of light sources and a plurality of detectors distributed among a plurality of modules, wherein each module comprises one or more of the light sources and one or more of the detectors; a manufactured calibration member made from a material that scatters light, the calibration member forming an exterior surface and configured to support the optical measurement device when the optical measurement device is placed on the calibration member; and a processing unit configured to: cause, while the optical measurement device is supported by the calibration member, at least one light source of the plurality of light sources to emit light toward the exterior surface of the calibration member and at least one detector of the plurality of detectors to detect arrival times for photons of the light after the light is scattered by the calibration member; and perform, based on the arrival times of photons, a calibration operation with respect to the optical measurement device.

An illustrative calibration assembly may include a manufactured calibration member made from a material that scatters light, the calibration member forming an exterior surface; and a shell made from a translucent material that allows light to pass therethrough, the shell forming an interior surface configured to be placed on the exterior surface of the calibration member and an exterior surface configured to support an optical measurement device when the optical measurement device is placed on the shell; wherein, while the optical measurement device is supported by the shell, the exterior surface of the calibration member is configured to scatter light emitted by the optical measurement device for performing a calibration operation with respect to the optical measurement device.

An illustrative manufactured calibration member may be made from a material that scatters light, the calibration member forming an arcuate exterior surface corresponding to an interior surface of an optical measurement device; wherein, while the optical measurement device is positioned on the calibration member, the exterior surface of the calibration member is spaced at a uniform distance away from the interior surface of the optical measurement device; wherein, while the optical measurement device is positioned about the calibration member, the exterior surface of the calibration member is configured to scatter light emitted by the optical measurement device for performing a calibration operation with respect to the optical measurement device.

An illustrative method may include causing, while an optical measurement device comprising a plurality of light sources and a plurality of detectors distributed among a plurality of modules is placed on a manufactured calibration member made from a material that scatters light, at least one light source of the plurality of light sources to emit light toward an exterior surface of the calibration member and at least one detector of the plurality of detectors to detect arrival times for photons of the light after the light is scattered by the calibration member; and performing, based on the arrival times of photons, a calibration operation with respect to the optical measurement device.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. Certain features of one embodiment described herein may be combined with or substituted for features of another embodiment described herein. For example, any embodiment can incorporate the shell described in relation to FIGS. 11-12B, the cover, heat source and/or light source described in relation to FIG. 14, the frame described in relation to FIGS. 15A-16B, and/or the anatomical features described in relation to FIG. 17. The description and drawings are accordingly to be regarded in an illustrative rather than a restrictive sense.

What is claimed is:

1. A system comprising:
   an optical measurement device comprising a plurality of light sources and a plurality of detectors distributed among a plurality of modules, wherein each module comprises one or more of the light sources and one or more of the detectors;
   a manufactured calibration member made from a material that scatters light, the calibration member forming an exterior surface and configured to support the optical measurement device when the optical measurement device is placed on the calibration member; and
   a processing unit configured to:
      cause, while the optical measurement device is supported by the calibration member, at least one light source of the plurality of light sources to emit light toward the exterior surface of the calibration member and at least one detector of the plurality of detectors to detect arrival times for photons of the light after the light is scattered by the calibration member; and
      perform, based on the arrival times of photons, a calibration operation with respect to the optical measurement device.

2. The system of claim 1, further comprising a frame forming a plurality of openings extending through the frame, wherein, while the frame is positioned on the calibration member, each opening of the plurality of openings of the frame is configured to receive a module of the plurality of modules of the optical measurement device.

3. The system of claim 1, further comprising a shell made from a translucent material that allows light to pass therethrough, the shell forming an interior surface configured to be placed on the exterior surface of the calibration member and an exterior surface configured to support the optical measurement device when the optical measurement device is placed on the shell.

4. The system of claim 1, further comprising a base attached to the calibration member and configured to support the calibration member.

5. The system of claim 1, further comprising a cover configured to cover the optical measurement device while the optical measurement device is positioned on the calibration member.

6. The system of claim 1, wherein the calibration member is dome-shaped.

7. The system of claim 1, wherein the exterior surface of the calibration member corresponds to an interior surface of the optical measurement device such that, while the optical measurement device is supported by the calibration member, the exterior surface of the calibration member is spaced at a uniform distance away from the interior surface of the optical measurement device.

8. The system of claim 1, wherein the calibration member is made from a light-absorbing material configured to absorb a first subset of photons of the light emitted by the at least one light source and reflect a second subset of photons of the light emitted by the at least one light source.

9. The system of claim 1, wherein an interior surface of the optical measurement device is positioned on the exterior surface of the calibration member while the optical measurement device is supported by the calibration member.

10. The system of claim 1, wherein the calibration member is made from a light-diffusing material configured to diffuse at least a portion of the light emitted by the at least one light source of the plurality of light sources within the calibration member.

11. The system of claim 1, wherein the performing the calibration operation includes determining an instrument response function associated with the optical measurement device.

12. The system of claim 11, wherein the determining the instrument response function includes:
   determining, based on the arrival times, a histogram associated with the optical measurement device; and
   designating the histogram as the instrument response function.

13. The system of claim 1, wherein the performing the calibration operation includes determining, with respect to the optical measurement device, one or more of: an instrument response function, a differential nonlinearity, a dark count rate, or a time delay associated with the detectors.

14. The system of claim 1, further comprising a light source configured to emit light toward at least one detector of the plurality of detectors of the optical measurement device.

15. The system of claim 1, further comprising a heat source configured to heat the optical measurement device for performing the calibration operation.

16. The system of claim 1, wherein the performing the calibration operation is based on emitting light from at least one light source of a first module toward the exterior surface of the calibration member and detecting, by at least one detector of a second module, arrival times for photons of the light after the light is scattered by the calibration member.

17. A calibration assembly comprising:
   a manufactured calibration member made from a material that scatters light, the calibration member forming an exterior surface; and
   a shell made from a translucent material that allows light to pass therethrough, the shell forming an interior surface configured to be placed on the exterior surface of the calibration member and an exterior surface configured to support an optical measurement device when the optical measurement device is placed on the shell;
   wherein, while the optical measurement device is supported by the shell, the exterior surface of the calibration member is configured to scatter light emitted by the optical measurement device for performing a calibration operation with respect to the optical measurement device.

18. The assembly of claim 17, further comprising a frame forming a plurality of openings extending through the frame, wherein, while the frame is positioned on the shell, each opening of the plurality of openings of the frame is configured to receive a module of the plurality of modules of the optical measurement device.

19. The assembly of claim 17, further comprising a base attached to the calibration member and configured to support the calibration member.

20. The assembly of claim 17, further comprising a cover configured to cover the optical measurement device while the optical measurement device is positioned on the shell.

21. The assembly of claim 17, wherein, while the optical measurement device is supported by the shell, the shell is configured to uniformly space the exterior surface of the calibration member from an interior surface of the optical measurement device.

22. The assembly of claim 17, further comprising a light source configured to emit light toward at least one detector of the optical measurement device.

23. The assembly of claim 17, further comprising a heat source configured to heat the optical measurement device for performing the calibration operation.

24. A manufactured calibration member comprising:
a material that scatters light; and
an arcuate exterior surface corresponding to an interior surface of an optical measurement device;
wherein, while the optical measurement device is positioned on the calibration member, the exterior surface of the calibration member is spaced at a uniform distance away from the interior surface of the optical measurement device;
wherein, while the optical measurement device is positioned about the calibration member, the exterior surface of the calibration member is configured to scatter light emitted by the optical measurement device for performing a calibration operation with respect to the optical measurement device.

25. The manufactured calibration member of claim 24, wherein the calibration member is dome-shaped.

26. The manufactured calibration member of claim 24, wherein the calibration member is made from a light-absorbing material configured to absorb a first subset of photons of the light emitted by the optical measurement device and reflect a second subset of photons of the light emitted by the optical measurement device.

27. The manufactured calibration member of claim 24, wherein the calibration member is made from a light-diffusing material configured to diffuse at least a portion of the light emitted by the optical measurement device within the calibration member.

28. A method comprising:
causing, while an optical measurement device comprising a plurality of light sources and a plurality of detectors distributed among a plurality of modules is placed on a manufactured calibration member made from a material that scatters light, at least one light source of the plurality of light sources to emit light toward an exterior surface of the calibration member and at least one detector of the plurality of detectors to detect arrival times for photons of the light after the light is scattered by the calibration member; and
performing, based on the arrival times of photons, a calibration operation with respect to the optical measurement device.

* * * * *